(12) United States Patent
Mazzocca et al.

(10) Patent No.: US 8,383,188 B2
(45) Date of Patent: Feb. 26, 2013

(54) HIGH STRENGTH SUTURE COATED WITH RGD PEPTIDE

(75) Inventors: Augustus D. Mazzocca, West Hartford, CT (US); Mary Beth McCarthy, Kensington, CT (US)

(73) Assignee: University of Connecticut, Farmington, CT (US)

( * ) Notice: Subject to any disclaimer, the term of this patent is extended or adjusted under 35 U.S.C. 154(b) by 42 days.

(21) Appl. No.: 13/186,054

(22) Filed: Jul. 19, 2011

(65) Prior Publication Data

US 2011/0274824 A1 Nov. 10, 2011

Related U.S. Application Data

(62) Division of application No. 11/845,683, filed on Aug. 27, 2007, now abandoned.

(60) Provisional application No. 60/840,467, filed on Aug. 28, 2006.

(51) Int. Cl.
*B05D 3/10* (2006.01)
*A61B 17/04* (2006.01)
*A61L 17/00* (2006.01)

(52) U.S. Cl. ........ 427/2.31; 427/2.1; 606/228; 606/229; 606/230; 606/231; 424/422; 424/423; 424/426

(58) Field of Classification Search .................. 427/2.1, 427/2.31; 606/228, 229, 231, 230; 424/422, 424/423, 426
See application file for complete search history.

(56) References Cited

U.S. PATENT DOCUMENTS

| | | | |
|---|---|---|---|
| 3,942,532 A | 3/1976 | Hunter et al. | |
| 3,949,755 A | 4/1976 | Vauquois | |
| 4,047,533 A | 9/1977 | Perciaccante et al. | |
| 4,321,038 A | 3/1982 | Porteous | |
| 4,344,908 A | 8/1982 | Smith et al. | |
| 4,411,854 A | 10/1983 | Maurer et al. | |
| 4,422,993 A | 12/1983 | Smith et al. | |
| 4,430,383 A | 2/1984 | Smith et al. | |
| 4,436,689 A | 3/1984 | Smith et al. | |
| 4,668,717 A | 5/1987 | Lemstra et al. | |
| 5,019,093 A | 5/1991 | Kaplan et al. | |
| 5,067,538 A | 11/1991 | Nelson et al. | |
| 5,234,764 A | 8/1993 | Nelson et al. | |
| 5,261,886 A | 11/1993 | Chesterfield et al. | |
| 5,266,327 A * | 11/1993 | Agrez | 424/426 |
| 5,278,063 A * | 1/1994 | Hubbell et al. | 435/402 |
| 5,314,446 A | 5/1994 | Hunter et al. | |
| 5,318,575 A | 6/1994 | Chesterfield et al. | |
| 5,383,925 A | 1/1995 | Schmitt | |
| 5,403,659 A | 4/1995 | Nelson et al. | |
| 5,540,703 A | 7/1996 | Barker, Jr. et al. | |

(Continued)

FOREIGN PATENT DOCUMENTS

EP 1 293 218 A1 3/2003

OTHER PUBLICATIONS

Gumusdereliogu et al. Biomodification of non-woven polyester fabrics by insulin and RGD for use in serum-free cultivation of tissue cells. Biomaterials 23 (202) pp. 3927-3935.*

(Continued)

*Primary Examiner* — Timothy Meeks
*Assistant Examiner* — Cachet Sellman
(74) *Attorney, Agent, or Firm* — Dickstein Shapiro LLP

(57) ABSTRACT

A high strength surgical suture material with improved tie down characteristics and tissue compliance formed of ultra-high molecular weight polyethylene (UHMWPE) yarns, the suture being coated with arginine-glycine-aspartate (RGD) peptide. The suture has exceptional strength, is ideally suited for most orthopedic procedures, and can be attached to a suture anchor or a curved needle.

1 Claim, 2 Drawing Sheets

U.S. PATENT DOCUMENTS

| | | |
|---|---|---|
| 5,630,976 A | 5/1997 | Nelson et al. |
| 5,720,765 A | 2/1998 | Thal |
| 6,045,571 A | 4/2000 | Hill et al. |
| 6,063,105 A | 5/2000 | Totakura |
| 6,716,234 B2 | 4/2004 | Grafton et al. |
| 7,029,490 B2 | 4/2006 | Grafton et al. |
| 2003/0050667 A1* | 3/2003 | Grafton et al. ............... 606/228 |
| 2005/0033362 A1 | 2/2005 | Grafton |
| 2006/0287676 A1* | 12/2006 | Prajapati et al. ............. 606/228 |

OTHER PUBLICATIONS

Hersel et al. RGD modified polymers: biomaterials for stimulated cell adhesion and beyond. Biomaterials 24 (2003) pp. 4385-4415.*

Du et al. 3D hepatocyte monolayer on hybrid RGD/galactose substratum. Biomaterials 2y7 (2006) pp. 5669-5980.*

Chen et al. The use of poly(1-lactide) and RGD modified microspheres for cell carriers in flow intermittency bioreactor for tissue engineering cartilage. Biomaterials 27y (2006) 4453-4460.*

\* cited by examiner

HIGH STRENGTH SUTURE COATED WITH RGD PEPTIDE

CROSS-REFERENCE TO RELATED APPLICATIONS

This is a divisional application of U.S. patent application Ser. No. 11/845,683, now abandoned, filed on Aug. 27, 2007, which claims priority to U.S. Provisional Application Ser. No. 60/840,467, filed on Aug. 28, 2006, the entire disclosures of which are hereby incorporated by reference.

FIELD OF THE INVENTION

The present invention relates to high strength surgical suture materials, and more particularly to braided suture blends of ultrahigh molecular weight polyethylene coated with RGD peptide.

DESCRIPTION OF THE RELATED ART

Suture strength is an important consideration in any surgical suture material. One of the strongest materials currently formed into elongated strands is an ultrahigh molecular weight long chain polyethylene, typically used for fishing line and the like, which is sold under the trade names Dyneema or Spectra. This material is much stronger than ordinary surgical suture, however, it does not have acceptable knot tie down characteristics for use in surgical applications.

BRIEF SUMMARY OF THE INVENTION

The present invention advantageously provides a high strength surgical suture material with improved tie down characteristics. The suture features a braided jacket made of ultrahigh molecular weight fibers. The suture is coated with arginine-glycine-aspartate (RGD) peptide. The ultrahigh molecular weight polyethylene provides strength. Polyester fibers woven with the high molecular weight polyethylene provide improved tie down properties. RGD peptide promotes cell adhesion to substrates in vivo by interacting with receptors, integrins, on cell surface proteins. Further, RGD peptides also increase the permeability of endothelial monolayers and therefore may aid in surgical applications.

In a preferred embodiment, the suture includes a multifilament jacket formed of ultrahigh molecular weight polyethylene fibers braided with polyester. The jacket surrounds a fiber core made substantially or entirely of ultrahigh molecular weight polyethylene. The core preferably includes three strands of ultrahigh molecular weight polyethylene, twisted at about three to six twists per inch.

The jacket preferably comprises eight strands of ultrahigh molecular weight polyethylene braided with six strands of polyester. The tinted strands can be included in black or some other contrasting color.

Ultrahigh molecular weight polyethylene fibers suitable for use in the present invention are marketed under the Dyneema trademark by Toyo Boseki Kabushiki Kaisha, and are produced in the U.S. by Honeywell under the trademark Spectra.

The suture of the present invention advantageously has the strength of Ethibond No. 5 suture, yet has the diameter, feel and tie-ability of No. 2 suture. As a result, the suture of the present invention is ideal for most orthopedic procedures such as rotator cuff repair, Achilles tendon repair, patellar tendon repair, ACL/PCL reconstruction, hip and shoulder reconstruction procedures, and replacement for suture used in or with suture anchors.

The suture is coated with RGD peptide. RGD peptide suitable for use in the present invention is marketed under PCI-36xx-PI by Peptides International, and under GRADSP peptide and GRGDSP peptide by Calbiochem. Other products suitable for use in the present invention marketed by Pierce are: (i) Product #28390—BupH MES Buffered Saline Packs to make a 500 ml of 0.1 M 2-[morpholino]ethanesulfonic acid, 0.9% NaCl, pH 4.7 when dissolved in 500 ml deionized water (5 liters total); (ii) Product #22980—1-Ethyl-3-[3-dimethylaminopropyl]carbodiimide hydrochloride (EDC or EDAC), a zero-length crosslinking agent used to couple carboxyl groups to primary amines and a water-soluble carbodiimide for rapid preparation of peptide conjugates; (iii) Product #24510—N-hydroxysulfosuccinimide (Sulfo-NHS), a product useful in improving the efficiency of EDC coupling.

A trace thread or two in the suture jacket aids surgeons in identifying the travel direction of the suture during surgery, particularly during operations viewed arthroscopically or remotely. Providing the trace threads in a regularly repeating pattern is particularly useful, allowing the surgeon to decode different ends of a length of suture, and to determine the direction of travel of a moving length of suture. The trace threads preferably are provided uniquely on each half of a length of suture to allow for tracing and identification of each end of the suture, such as when the suture is threaded through an eyelet of a suture anchor.

Other features and advantages of the present invention will become apparent from the following description of the invention which refers to the accompanying drawings.

DETAILED DESCRIPTION OF THE INVENTION

The term "yarn(s)," as used herein, is to be understood as including fiber(s), filament(s), and the like used to make a suture of the present invention. Typically, though, yarns are comprised of fibers and/or filaments.

Figure 1:
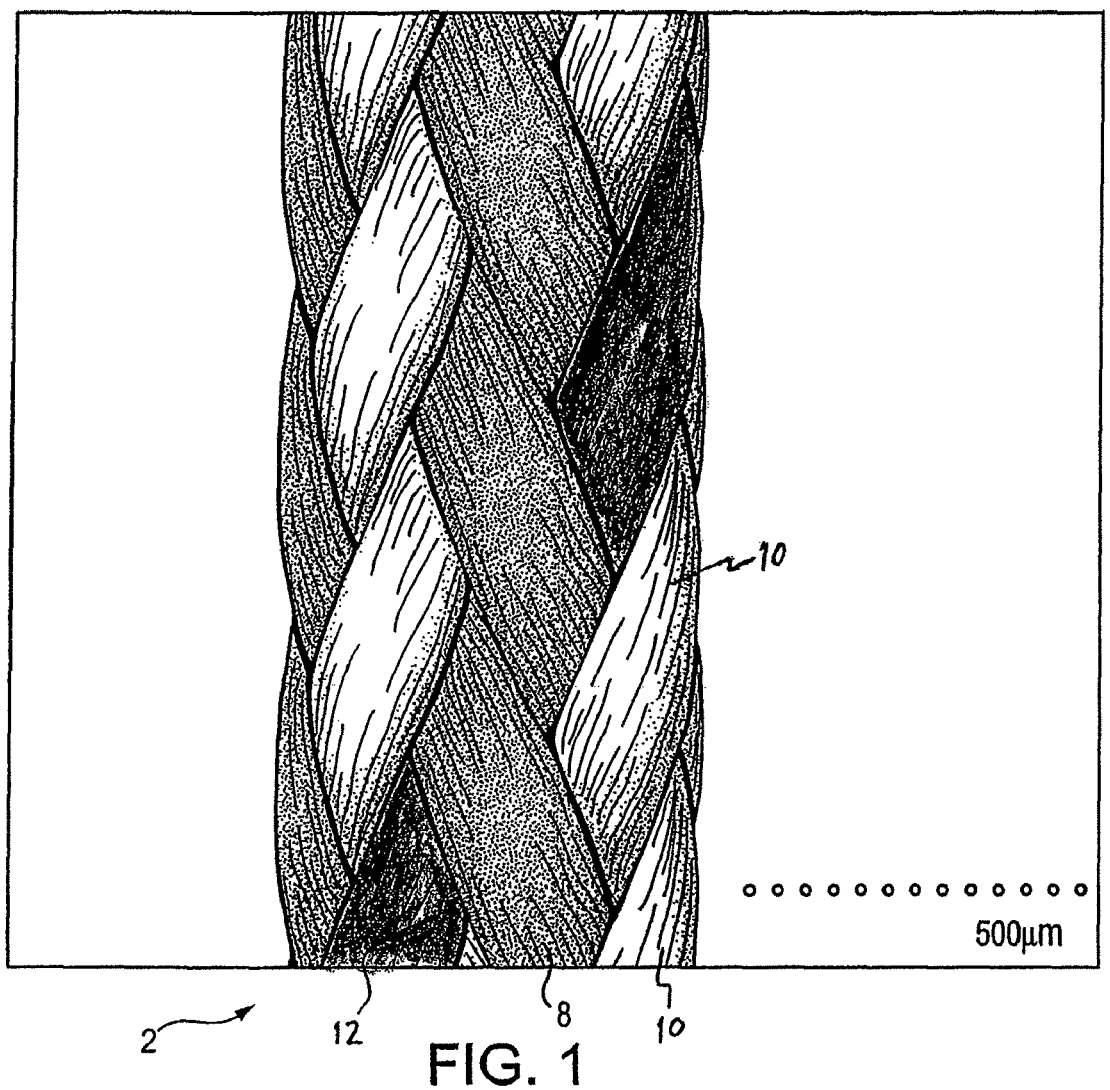
FIG. 1 is a copy of a scanning electron micrograph of a length of suture according to the present invention.
Figure 2:
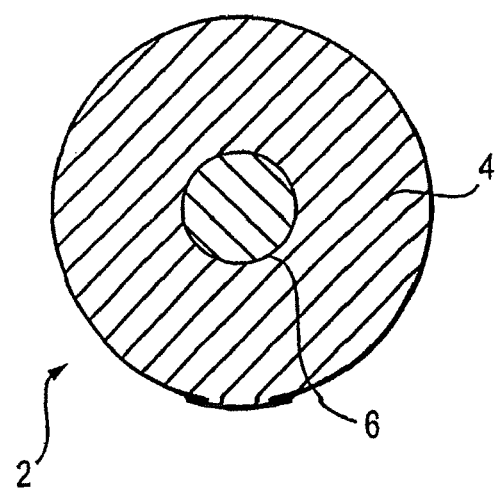
FIG. 2 is a schematic cross section of a length of suture according to the present invention.

Referring to FIG. 1, a scanning electron micrograph of a length of suture 2 according to the present invention is shown. Suture 2 is made up of a jacket 4 and a core 6 surrounded by the jacket 4. See FIG. 2. Strands of ultrahigh molecular weight polyethylene (UHMWPE) 8, such as that sold under the tradenames Spectra and Dyneema, strands of polyester 10, and tinted strands 12 are braided together to form the jacket 4. Core 6 is formed of twisted strands of UHMWPE.

UHMWPE, used for strands 8, is substantially translucent or colorless. The polyester strands 10 are white (undyed). Due to the transparent nature of the UHMWPE, the suture takes on the color of strands 10 and 12, and thus appears to be white with a trace in the contrasting color.

In accordance with the present invention, trace strands 12 are preferably provided in black. The black trace assists surgeons in distinguishing between suture lengths with the trace and suture lengths without the trace. Traces also assist the surgeon in identifying whether the suture is moving. The trace can extend the entire length of the suture or only on half of a length of suture, the other half of the suture length remaining plain (white). Alternatively, the traces can form visibly distinct coding patterns on each half of the suture length. As a result, when the suture is threaded through the eyelet of a suture anchor, for example, the two legs (halves) of the length of suture are easily distinguished, and their direction of travel will be readily evident when the suture is pulled during surgery.

Details of the present invention will be described further below in connection with the following examples:

EXAMPLE

USP Size 5 (EP Size 7)

Made on a 16 carrier Hobourns machine, the yarns used in the braided jacket are Honeywell Spectra 2000, polyester type 712, and nylon. The jacket is formed using eight strands of 144 decitex Spectra per carrier, braided with six strands of 100 decitex polyester, and two strands of tinted nylon. The core is formed of three carriers of 144 decitex Spectra braided at three to six twists per inch. A No. 5 suture is produced.

To make various sizes of the inventive suture, different decitex values and different PPI settings can be used to achieve the required size and strength needed. In addition, smaller sizes may require manufacture on 12 carrier machines, for example. The very smallest sizes can be made without a core. Overall, the suture may range from 5% to 90% ultrahigh molecular weight polymer (preferably at least 40% of the fibers are ultrahigh molecular weight polymer), with the balance formed of polyester and/or nylon. The core preferably comprises 18% or greater of the total amount of filament.

The suture is coated with RGD peptide (PCI-36xx-PI). The RGD peptide-coating increases permeability of endothelial monolayers, thereby resulting in a decrease in abrasion resistance to the suture. RGD peptides promote cell adhesion to substrates in vivo by interacting with receptors, integrins, on cell surface proteins and thus, RGD peptide-coated sutures perform better than other sutures in surgical applications.

Peptides may be coupled to or adsorbed to the suture. Typically, about 500 ml of coupling buffer, e.g., about 0.1M MES buffer, is prepared and a base, for example NaOH, is used to lower the acidity of the coupling buffer to a pH value of about 6.0.

In one embodiment of the present invention, peptides are coupled to a suture. For coupling peptides to a suture, the suture is cut into 6 inch strips and soaked into an MES buffer for at least 30 minutes. Later, acid hydrolysis is performed, i.e., the suture is taken from the MES buffer and quickly dipped into an acid medium, for example, about 15 ml of 6N HCl and about 200 ul of $H_2O_2$. Thereafter, the suture is immediately put back into the MES buffer and washed several times. EDC and sulfo-NHS buffers are added to the MES buffer, for example, about 36 mg of EDC and about 99 mg of sulfo-NHS is added to about 90 ml of MES buffer.

The suture is removed from the MES buffer and placed into the EDC buffer for about 15 minutes. The suture is then washed three times with the MES buffer. About 2 ml of peptide solution is immediately prepared and the suture immersed in the peptide solution. The peptide is allowed to react on the suture at 4° C. The suture is then washed about five times with MES buffer and then allowed to air dry under a hood.

In another embodiment of the present invention, peptides are adsorbed to a suture. For adsorbing peptides to a suture, the suture is cut into 6 inch strips and soaked in a MES buffer for at least 30 minutes. Later, the suture is taken out and immediately placed back into the MES buffer and washed about three times. About 2 ml of peptide solution is immediately prepared and the suture immersed in the peptide solution. The peptide is allowed to react on the suture at 4° C. The suture is then washed about five times with MES buffer and then allowed to air dry under the hood.

In an alternative embodiment of the present invention, a partially bioabsorbable suture is provided by blending a high strength material, such as UHMWPE fibers, with a bioabsorbable material, such as PLLA or collagen, for example. Accordingly, a suture made with about 10% Spectra or Dyneema blended with absorbable fibers would provide greater strength and with less stretch. Over time, 90% or more of the suture would absorb, leaving only a very small remnant of the knot. The absorbable suture can include coatings, for example collagen.

The ultra high molecular weight (UHMW) polymer component of the present invention provides strength, and the polyester component is provided to improve tie ability and tie down characteristics. However, it has been found that the UHMW polymer provides an unexpected advantage of acting as a cushion for the polyester fibers, which are relatively hard and tend to damage each other. The UHMW polymer prevents breakage by reducing damage to the polyester when the suture is subjected to stress.

Figure 3:
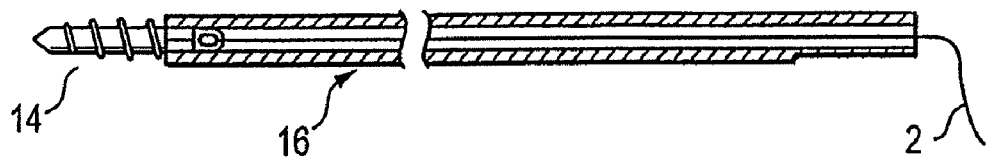
FIG. 3 is an illustration of the suture of the present invention attached to a suture anchor loaded onto a driver.
Figure 4A:
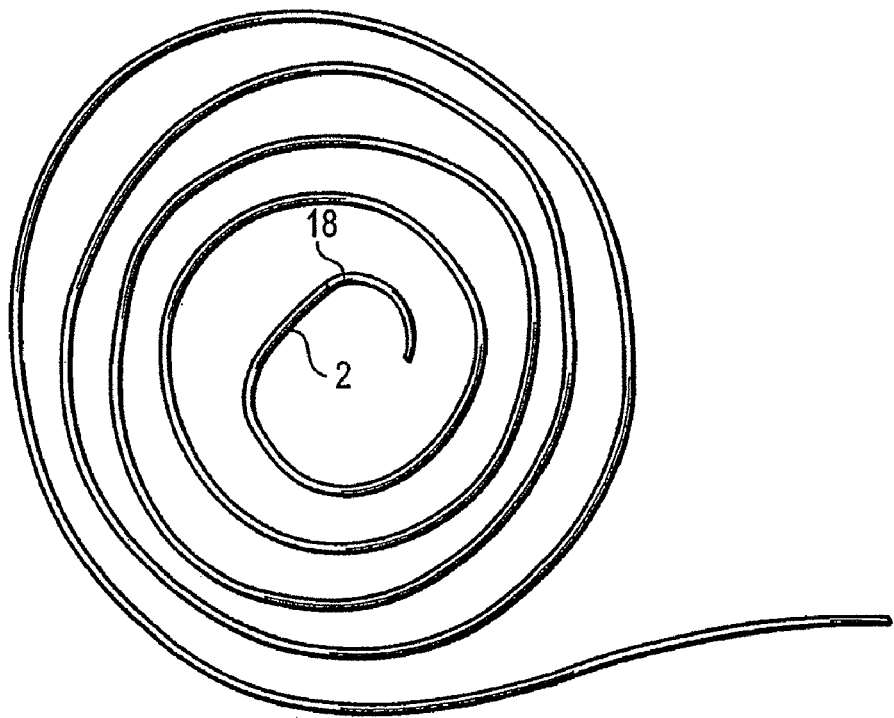
FIGS. 4A and 4B show the suture of the present invention attached to a half round, tapered needle.
Figure 4B:
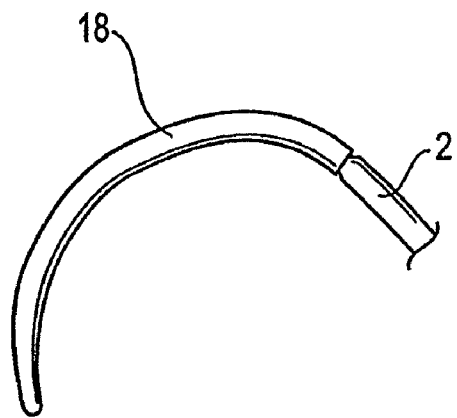

In one method of using the suture of the present invention, the suture 2 is attached to a suture anchor 14 as shown in FIG. 3 (prepackaged sterile with an inserter 16), or is attached at one or both ends to a half round, tapered needle 18 as shown in FIGS. 4A and 4B. FIG. 4A also illustrates a length of suture having regularly repeating pattern of trace threads according to the present invention. Sections of the length of suture 2 have tinted tracing threads woven in. The alternating patterned and plain sections aid the surgeon in determining the direction of suture travel when pulling the suture, for example.

Although the present invention has been described in relation to particular embodiments thereof, many other variations and modifications and other uses will become apparent to those skilled in the art.

What is claimed is:

1. A process for making a suture comprising a jacket comprising a plurality of braided yarns of ultrahigh molecular weight polyethylene coated with arginine-glycine-aspartate (RGD) peptide, comprising the steps of:
   soaking the suture in a MES buffer;
   removing the suture from the MES buffer, performing acid hydrolysis on the suture, and subsequently placing the suture back in the MES buffer;
   removing the suture from the MES buffer and placing the suture into a MES buffer comprising 1-ethyl-3-(3-dimethylaminopropyl) carbodiimide (EDC) and N-hydroxysulfosuccinimide (sulfo-NHS); and
   washing the suture with the MES buffer comprising EDC and sulfo-NHS and immersing the suture into a RGD peptide solution to allow peptides to couple to the suture to form the RGD peptide coated suture.

* * * * *